(12) United States Patent
Moreno Rodríguez

(10) Patent No.: US 12,063,978 B2
(45) Date of Patent: Aug. 20, 2024

(54) APPARATUS FOR CONTROLLING A VAPOUR GENERATING DEVICE

(71) Applicant: JT International S.A., Geneva (CH)

(72) Inventor: Juan José Moreno Rodríguez, Geneva (CH)

(73) Assignee: JT International S.A. (CH)

( * ) Notice: Subject to any disclaimer, the term of this patent is extended or adjusted under 35 U.S.C. 154(b) by 750 days.

(21) Appl. No.: 17/255,181

(22) PCT Filed: Jun. 28, 2019

(86) PCT No.: PCT/EP2019/067319
§ 371 (c)(1),
(2) Date: Dec. 22, 2020

(87) PCT Pub. No.: WO2020/007726
PCT Pub. Date: Jan. 9, 2020

(65) Prior Publication Data
US 2021/0259318 A1 Aug. 26, 2021

(30) Foreign Application Priority Data

Jul. 3, 2018 (EP) .................................. 18181438

(51) Int. Cl.
*A24F 40/53* (2020.01)
*A24F 40/10* (2020.01)
(Continued)

(52) U.S. Cl.
CPC .............. *A24F 40/53* (2020.01); *A24F 40/10* (2020.01); *A24F 40/65* (2020.01); *G06K 19/0723* (2013.01)

(58) Field of Classification Search
CPC .......... A24F 40/53; A24F 40/10; A24F 40/65; A24F 40/46; G06K 19/0723;
(Continued)

(56) References Cited

U.S. PATENT DOCUMENTS

2002/0010603 A1* 1/2002 Doi .................... G06Q 30/0235
340/5.2
2006/0133831 A1* 6/2006 Rommelmann ... G03G 21/1892
399/12
(Continued)

FOREIGN PATENT DOCUMENTS

CN 105792687 A 7/2016
CN 107205469 A 9/2017
(Continued)

OTHER PUBLICATIONS

International Search Report for Application No. PCT/EP2019/067319 mailed Sep. 26, 2019, 3 pages.
(Continued)

*Primary Examiner* — Alexander Gilman
(74) *Attorney, Agent, or Firm* — Lerner David LLP

(57) ABSTRACT

An apparatus for controlling a vapour generating device, which generates vapour through use of a consumable, includes a data storage medium and a communication means for communicating with the device. The data storage medium is arranged to store data associated with control of activation of the device and data associated with control of the vapour generating device in use. The communication means communicates with the device such that, in use, both activation and operation of the device can be controlled based on the stored data.

14 Claims, 2 Drawing Sheets

(51) Int. Cl.
*A24F 40/65* (2020.01)
*G06K 19/07* (2006.01)

(58) Field of Classification Search
CPC .......... A61M 2205/52; A61M 2209/06; A61M 15/06; A61M 11/042; A61M 15/008; A61M 2205/273; A61M 2209/01; A61M 15/0081; A61M 2205/276; A61M 2205/3576
USPC ........................................................ 131/329
See application file for complete search history.

(56) References Cited

U.S. PATENT DOCUMENTS

| | | | | |
|---|---|---|---|---|
| 2014/0246035 | A1* | 9/2014 | Minskoff | A24F 40/65 131/329 |
| 2015/0142387 | A1* | 5/2015 | Alarcon | A24F 40/53 702/187 |
| 2016/0143361 | A1* | 5/2016 | Juster | A24F 40/65 392/404 |
| 2016/0157524 | A1* | 6/2016 | Bowen | G01N 33/0027 702/50 |
| 2016/0211693 | A1* | 7/2016 | Stevens | H04W 48/16 |
| 2016/0324217 | A1* | 11/2016 | Cameron | G08C 17/02 |
| 2016/0325055 | A1* | 11/2016 | Cameron | A24F 40/50 |
| 2016/0338407 | A1* | 11/2016 | Kerdemelidis | A24F 40/60 |
| 2016/0363570 | A1* | 12/2016 | Blackley | A61M 15/0003 |
| 2017/0006917 | A1* | 1/2017 | Alvarez | A24F 40/42 |
| 2017/0018000 | A1* | 1/2017 | Cameron | G06Q 30/0269 |
| 2017/0020188 | A1* | 1/2017 | Cameron | A24F 40/60 |
| 2017/0020191 | A1* | 1/2017 | Lamb | A61M 15/06 |
| 2017/0020196 | A1* | 1/2017 | Cameron | A24F 40/50 |
| 2017/0028178 | A1* | 2/2017 | Skoda | G16H 40/67 |
| 2017/0042230 | A1* | 2/2017 | Cameron | A24F 40/60 |
| 2017/0099877 | A1* | 4/2017 | Worm | A61M 15/0023 |
| 2017/0238606 | A1* | 8/2017 | Matsumoto | A24F 42/00 |
| 2017/0266397 | A1* | 9/2017 | Mayle | A61M 15/06 |
| 2017/0304563 | A1* | 10/2017 | Adelson | A61M 15/003 |
| 2017/0368273 | A1* | 12/2017 | Rubin | A61M 16/0093 |
| 2018/0146708 | A1* | 5/2018 | Batista | A24F 40/53 |
| 2018/0184722 | A1 | 7/2018 | Murison et al. | |
| 2018/0296779 | A1* | 10/2018 | Takeuchi | A61M 11/042 |

FOREIGN PATENT DOCUMENTS

| | | |
|---|---|---|
| CN | 107624040 A | 1/2018 |
| CN | 108025151 A | 5/2018 |
| JP | 2002032805 A | 1/2002 |
| JP | 2006171768 A | 6/2006 |
| JP | 2014500017 A | 1/2014 |
| KR | 20180044978 A | 5/2018 |
| WO | 2012065754 A2 | 5/2012 |
| WO | 2015077646 A1 | 5/2015 |
| WO | 2016076178 A1 | 5/2016 |
| WO | 2017109868 A1 | 6/2017 |
| WO | 2017148829 A1 | 9/2017 |
| WO | 2017205692 A1 | 11/2017 |

OTHER PUBLICATIONS

Search Report dated Jul. 27, 2022 from the Office Action for Chinese Application No. 201980044983 X issued Aug. 2, 2022, 2 pages.

* cited by examiner

APPARATUS FOR CONTROLLING A VAPOUR GENERATING DEVICE

CROSS-REFERENCE TO RELATED APPLICATIONS

The present application is a national phase entry under 35 U.S.C. § 371 of International Application No. PCT/EP2019/067319, filed Jun. 28, 2019, published in English, which claims priority to European Application No. 18181438.5 filed Jul. 3, 2018, the disclosures of which are incorporated herein by reference.

BACKGROUND OF THE INVENTION

The present invention relates to an apparatus for controlling a vapour generating device, together with a system comprising a vapour generating device and a consumable for the device.

Vapour generating devices which generate vapour through heating of a consumable are well-known and are becoming increasingly popular. Such devices will often heat a solid material, such a tobacco, or a liquid with a flavour generating component to generate a vapour for inhalation by a user. Such devices have the advantage of generating an inhalable vapour without requiring burning of the consumable. In such devices it is preferable for heating to occur for only a certain period or for only a specified amount of consumable to be heated at any one time so that the experience can be tailored to suit the user.

Such devices are generally utilised by a user at different times and for variable intervals throughout the day. Smoking devices must therefore be suitable to control the heating and preferably monitor consumable usage to ensure high quality vapour generation. Furthermore there is a need for control of the type of consumable that is inserted into the device so as to ensure only approved and safety tested consumables are used, and so that the device can safely and reliably operate in accordance with the type of consumable inserted therein.

Accordingly there is a need for an apparatus which can improve the reliability and safety of operation of a vapour generating device to ensure safe and reliable use by a consumer. The present invention seeks to provide this.

BRIEF SUMMARY OF THE INVENTION

According to a first aspect of the present invention there is provided an apparatus for controlling a vapour generating device which generates vapour through use of a consumable, the apparatus comprising:

a data storage medium arranged to store data associated with control of activation of the device and data associated with control of the vapour generating device in use; and communication means for communicating with the device such that, in use, both activation and operation of the device can be controlled based on the stored data.

The apparatus may comprise a part of the device in which case the apparatus may be a part of a controller for the device and the communication means for communicating with the device may simply be internal means for reading the data stored on the data storage medium and for sending control signals to a vapour generating unit of the device (e.g. a wire which is selectively connectable to a battery).

In such a case, the communication means may also communicate with an identifier associated with the consumable. For example, it may communicate with a data storage medium included in a package containing a plurality of consumables, which data storage medium includes identification data associated with the plurality of consumables contained in the package.

The present invention has the benefit of being able to retain data which controls both the activation of the device and operation of the device while using the consumable such that only safe consumables can be employed and the safety of the use the consumable can be controlled effectively.

The data associated with operation of the device may include data relating to an operation related to consumable consumption. This data may be least one of: operation time of a heater associated with the vapour generating device, operating temperature of a heater associated with the vapour generating device; a puff detection sensor in the vapour generating device; a consumable level detector in the vapour generating device; a battery consumption and/or charge level detector in the vapour generating device; and a device for detecting replacement of the consumable within the vapour generating device.

With this aspect of the invention it is possible to ensure optimum control of the vapour generating device to ensure safe and reliable vapour generation.

The data relating to operation of the vapour generating device may further comprise data defining the period of time or number of activations that the vapour generating device is allowed to have.

This aspect of the invention has the benefit of ensuring that a consumable is only used over a reliable and predictable timeframe or for a predetermined number of times, which is selected to ensure optimum quality of vapour generation as well as safety.

The apparatus may be arranged such that, once the data stored in the data storage medium has been used to provide control to the vapour generating device the data is prevented from being used again.

This feature of the invention restricts the apparatus from being used multiple times and therefore restricts the possibility of it being employed to allow the use of unsafe or counterfeit consumer material.

The apparatus may be arranged such that the data associated with activation of the vapour generating device or the data associated with control of the vapour generating device in use allows control of a first counter which counts the level of usage of a consumable for one vapour generating session and prevents operation of the device after a predetermined level of usage of the consumable for one vapour generating session and reset of the first counter once data relating to a replacement consumable is provided.

Examples of the data relating to a replacement consumable are data from consumable detecting sensor, data from heating chamber lid open/close detecting sensor, and data from a heating controller that a heating session is finished.

The examples of the level of usage are a period of heater operation time, puff counts, and the level of battery consumption.

One vapour generating session corresponds to the appropriate session provided by the amount of consumable which can be appropriately installed in a chamber in which the consumable generates vapour.

This feature of the invention restricts the vapour generating device from being used for more than a predetermined level of usage for one consumable or a certain amount of consumable material which is for one vapour generating session. This ensures that a user can use consumables that are in good condition.

The apparatus may be arranged such that the data associated with activation of the vapour generating device or the data associated with control of the vapour generating device in use allows control of a second counter which counts the number of consumables that have been used by the device such that the vapour generating device can be used only for a predetermined, fixed, number of consumables until the second counter is reset by the provision of new data associated with control of activation of the device or data associated with control of the vapour generating device in use, or which counts the level of usage of consumables for plural smoking session that have been used by the device such that the vapour generating device can be used only for a predetermined, fixed, usage of consumables until the second counter is reset by a provision of new data associated with control of activation of the vapour generating device or data associated with control of the vapour generating device in use.

These aspects of the present invention ensure that the device can only be used for a certain fixed i.e.: one or fixed plural number, or amount of consumables for plural vapour generating sessions before data in the apparatus inhibits use of the device. It may be convenient to provide an over-ride function whereby the user can over-ride the inhibition of the device to permit a malfunction of the device to be corrected. It may be convenient if such an over-ride function can only be operated by the user for a predetermined number of times before requiring the user to seek intervention from a help function (e.g. a customer services centre associated with the manufacturer or distributer, etc.) in order to re-enable further over-rides.

The apparatus may be arranged such that the data stored thereon is rewritable. This enables updating of the data to ensure safe operation and reduces the requirement for a high capacity data storage medium.

The invention also provides a system comprising the apparatus defined above, a vapour generating device for receiving signals from the apparatus, and at least one consumable from which the vapour generating device generates vapour in use.

With this system the apparatus may be provided on packaging for the at least one consumable or in material placed in the packaging, which ensures reliable data transfer and ease of manufacture. It also enables the packaging to be flexible in design so that consumer information can be provided in conjunction with the apparatus if required. Further the user does not need to have additional components dedicated to provide the apparatus.

The consumable may comprise at least one of: tobacco, nicotine-containing vaporizable liquid, or vaporizable liquid which does not contain nicotine.

The apparatus may be formed as part of an RFID tag which communicates wirelessly with the vapour generating device to provide the control data thereto. This ensures reliable data transfer and again is simple to manufacture.

The system may be arranged such that the vapour generating device has control means for controlling components on the vapour generating device based on data communicated from the apparatus. This ensures optimum control of the device.

The system may be arranged such that the vapour generating device has identifying means for identifying the presence of a consumable placed therein, a second counter for counting the sequential number of consumables that have been placed therein or the level of usage of the consumable for plural vapour generating sessions and/or a first counter for counting the level of usage of the consumable for one vapor generating session, and control means for controlling vapour generation which may operate in dependence upon the outputs of the identifying means and the counters. This ensures effective but simple control of the device with a low cost apparatus that is easy to implement.

According to a second aspect of the present invention, there is provided a system comprising a vapour generating device and a package containing a plurality of consumable items (consumables), wherein the device includes a vapour generating unit and a device controller, the device controller including a device data store, and wherein the package includes a package data storage medium for storing device control data, and wherein the vapour generating device further includes a package data storage medium reader, for reading the data stored on the package data storage medium and for updating device control data stored in the device data store in accordance with the read data, and wherein the controller is operable to control operation of the device (including at least controlling operation of the vapour generating unit) in dependence upon the updated device control data stored in the device data store, and for further updating the device control data stored in the device data store in dependence upon the controlled operation of the device.

Preferably, the device control data is used to control some aspect of the amount of operation which the device is able to perform. For example, the device could estimate how much operation of the device should be performed to enable a consumable to be fully consumed and limit the total amount of operation to that required to consume all of the consumables contained with the package of consumables. Additionally, once the device determines that sufficient operation of the device has occurred for a consumable item to be fully consumed, it may indicate to the user that the consumable currently in use should be replaced with a new consumable. A sensor for sensing the opening of a door that gives access to an oven portion can be used as an indication that a consumable has been replaced by a new consumable. Thus, for example, by monitoring the number of times that a door is opened to give access to an oven portion of the device designed to receive a consumable and monitoring the amount of time during which the vapour generating unit is operating to generate vapour it may be possible to estimate when the user has consumed all of the consumables contained in the packaging and to prevent further usage of the device until the device has been updated with new data obtained from a new package of consumables. In this way the user is discouraged from attempting to vaporise consumable portions other than those sold for use with the device.

Preferably, the consumables are composed of decomposable organic matter which can be disposed of in an environmentally safe manner with minimum adverse impact on the environment. For example, the consumable may be a portion of tobacco, or a portion of processed tobacco including humectants such as vegetable glycerine and/or propylene glycol and possibly further including safe-to-ingest items such as polysaccharides, flavourings, gel-forming agents etc. Such consumable items are not well adapted to include sophisticated data storage mediums such as (Radio Frequency IDentification) RFID tags. Moreover, including such components on the consumables increases their adverse impact on the environment when disposed of and can cause issues if heated in a device which includes an oven for heating the consumable in order to generate a vapour therefrom.

Preferably, the package data storage medium comprises an RFID tag (preferably a passive RFID tag) and the package data storage medium reader, for reading the data stored on the RFID tag comprises an RFID reader. In such a case it is also preferred if the RFID reader is also capable of writing to the RFID tag such that once a package has been read by a device, the device is updated to add data (e.g. "use credits") associated with the device, and at the same time, the RFID tag on the package is also updated (e.g. to remove those use credits from the RFID tag) so that the tag can no longer (or not again) be used to update a device to permit a certain amount of operation.

If the package data storage medium is not an RFID tag, it may be inconvenient to write new data to it after it has been used to authorise a device to operate for a predetermined amount of time. A package with such a data storage medium may be termed a read-only package. For example, the package data storage medium may simply be a printed indicia such as a bar code. In such a case, it is preferred if the printed indicia is unique for each package and, moreover, if it includes some encrypted data by which the indicia may be authenticated (e.g. only if a secret key is known by the device can it decrypt the data and compare this with some aspect of the rest of the indicia, etc.). Once the device has read a package it may store the identity of the package which it has read so that it will not again update its data to permit further operation of the device based on a second or subsequent reading of the same package.

In the case of a read-only package, it may be advantageous to provide a (vapour generating) device which includes a communication means for establishing a data connection with a remote device (e.g. a remote server), for example, via a portable user device such as a "smart-phone". In this way, the device may communicate with a remote server whenever a read-only package is read, which remote server may store details of "spent" packages.

When reading a "new" package the device can query the remote server with details of the package ID to ascertain if it has already been used. If it has, the device may not update its data storage to allow a certain amount of operation of the device (and it may inform the user accordingly via a suitable user interface (e.g. via the smart phone)). If, on the other hand, the remote server reports that that package ID has not yet been used, then the device will update its data store to permit a predetermined amount of operation of the device and the server will update its records so that it will not approve any subsequent re-readings of that package ID, etc.

Alternatively, where the device is able to communicate with, for example, a remote server via, for example, a smartphone, it may be convenient if a user can purchase a new package of consumables via the smartphone and the details of the package purchased can be used to update the associated vapour generating device that such a package of consumables has been purchased. In such a case the user may then specify to the vapour generating device (e.g. via and "app" or similar functionality using the smartphone or similar device such as a computer) which type of consumable, out of possibly multiple different types associated with multiple different purchased packages) has been or is going to be installed by the user into the device, etc.

It is preferred if the device can control both the amount of operation of the vapour generating unit and certain control settings for its operation (e.g. a heating temperature (possibly together with a heating duration), or a temperature profile (i.e. a sequence of heating temperatures over a period of time), specific for the particular consumable items contained within the packaging based on the data read from the package data storage medium.

According to a further aspect of the present invention, there is provided a system comprising a vapour generating device and a package containing a plurality of consumable items (consumables), wherein the device includes a vapour generating unit and a device controller, the device controller including a device data store, and wherein the package includes an apparatus for controlling the vapour generating device, the apparatus including a package data storage medium for storing device control data, and wherein the vapour generating device further includes a package data storage medium reader, for reading the data stored on the package data storage medium and for updating device control data stored in the device data store in accordance with the read data, and wherein the controller is operable to control operation of the device (including at least controlling operation of the vapour generating unit) in dependence upon the updated device control data stored in the device data store, and for further updating the device control data stored in the device data store in dependence upon the controlled operation of the device.

According to another aspect of the present invention, there is provided a vapour generating device control apparatus which generates vapour through use of a consumable, the apparatus comprising:

a data storage medium arranged to store data used for control of activation of the device and data used for control of the vapour generating device in use; and communication unit for communicating with the device such that, in use, both activation and operation of the device can be controlled by the apparatus based on the stored data.

Preferably, the communication unit of the apparatus further communicates with the consumable. Alternatively, the communication means of the apparatus further communicates with an identifier of the consumable.

Preferably, the data used for control of the device includes data used for a consumable consumption operation.

Preferably, the consumable consumption operation is at least one of: operation time of a heater of the vapour generating device; operating temperature of a heater of the vapour generating device; a puff detection sensor in the vapour generating device; a consumable level detection in the vapour generating device; a battery consumption and/or charge level detection in the vapour generating device; and a detection of replacement of the consumable within the vapour generating device.

Preferably, the data used for control of the vapour generating device further comprises data defining the period of time or number of activations that the vapour generating device is allowed to have.

Preferably, the apparatus is arranged such that, once the data stored in the data storage medium has been used for control of the vapour generating device the data is prevented from being used again. This may be achieved by deleting the data, transferring the data to an inaccessible area of the data storage medium and rewriting the data such that it cannot be used again once the data has been used for control of the device. Other methods of preventing the data from being used again will be readily apparent to the skilled person.

Preferably, the data used for activation of the vapour generating device or the data used for control of the vapour generating device in use allows control of a first counter which counts the level of usage of a consumable for one vapour generating session and allows operation of the device to be prevented after a predetermined level of usage of the consumable for one vapour generating session and rest of the first counter once data relating to a replacement consumable is provided.

An example of preventing operation of the device is to disable, temporarily or permanently, the function of vapour generation by disabling the heater or atomizer of the device. Another example would be to prevent the consumable access to the heating chamber or equivalent feature by, for instance, locking a lid of the heating chamber. Further examples of preventing device operation include blocking an air supply to components of the device such as the heating chamber, or by blocking airflow between components such as the heating chamber and mouthpiece. Yet another example of preventing operation is to lock a user interface of the device to stop the device from being activated. Other examples will be readily apparent to the skilled person.

Preferably, the data used for activation of the vapour generating device or the data used for control of the vapour generating device in use allows control of a second counter which counts the number of consumables that have been used by the device such that vapour generating device can be used only for a predetermined number of consumables until the second counter is reset by the provision of a new data used for control of activation of the device or data used for control of the vapour generating device in use, or which counts the level of usage of consumables for plural vapour generating sessions that have been used by the device such that the vapour generating device can be used only for a predetermined, fixed, usage of consumables until the second counter is reset by a provision of new data used for control of activation of the device or data used for control of the vapour generating device in use.

Preferably, the apparatus is arranged such that the data stored on the data storage medium is rewritable.

This aspect of the invention also provides a system comprising the apparatus defined above in this aspect, a vapour generating device for receiving signals from the apparatus, and at least one consumable from which the vapour generating device generates vapour in use.

Preferably, the apparatus of the system is provided on packaging for the at least one consumable or a material attached in the packaging.

Preferably, the at least one consumable comprises at least one of: tobacco, nicotine-containing vaporizable liquid, or vaporizable liquid which does not contain nicotine.

Preferably, the apparatus of the system is formed as part of a Radio Frequency Identification, RFID, tag which communicates wirelessly with the vapour generating device to provide the control data to the vapour generating device.

Preferably, the vapour generating device has a control unit for controlling components on the vapour generating device based on data communicated from the apparatus.

Preferably, the vapour generating device has a first counter for counting the level of usage of a consumable for one vapour generating session, a second counter for counting the sequential number of consumables that have been placed in the device or the level of usage of the device for a plurality of vapour generating sessions, and the control unit further controls vapour generation in dependence upon the counters.

BRIEF DESCRIPTION OF THE DRAWINGS

Examples of the present invention will now be described with reference to the accompanying drawings, in which.

DETAILED DESCRIPTION

Figure 1:
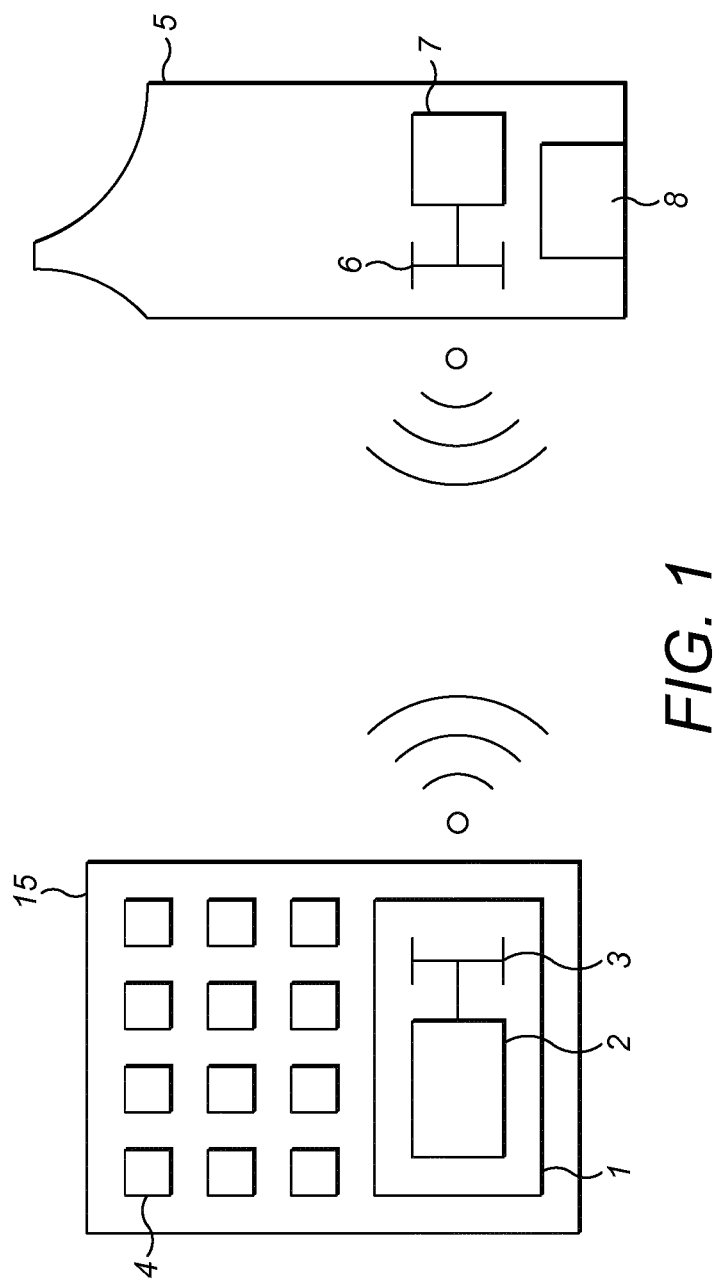
FIG. 1 is a schematic diagram showing a system employing an apparatus according to the present invention.

Referring to FIG. 1, an apparatus 1 according to the present invention is, in this example, provided in the form of an RFID tag with a processing and data storage component 2 and antenna 3. In this example the apparatus 1 is configured to be applied to packaging 15, in the form of a case, which holds consumable product 4. In this example the consumable product is a pouch tobacco, cut tobacco, foam tobacco or rod of tobacco which can be heated to generate vapour. However, it will be appreciated that other forms of consumables, such as pouches of another type of heatable material, or containers of vaporizable liquid can be provided. It will also be appreciated that, whilst in this example the apparatus is in the form of an RFID tag, other forms can be taken such as circuitry formed within packaging or each individual consumable as required.

A system according to the invention comprises the apparatus 1 in combination with consumable product 4 and a vapour generating device 5. As shown in FIG. 1, the vapour generating device comprises, in this example, an antenna 6, control circuitry 7 and a heater 8.

Figure 2:
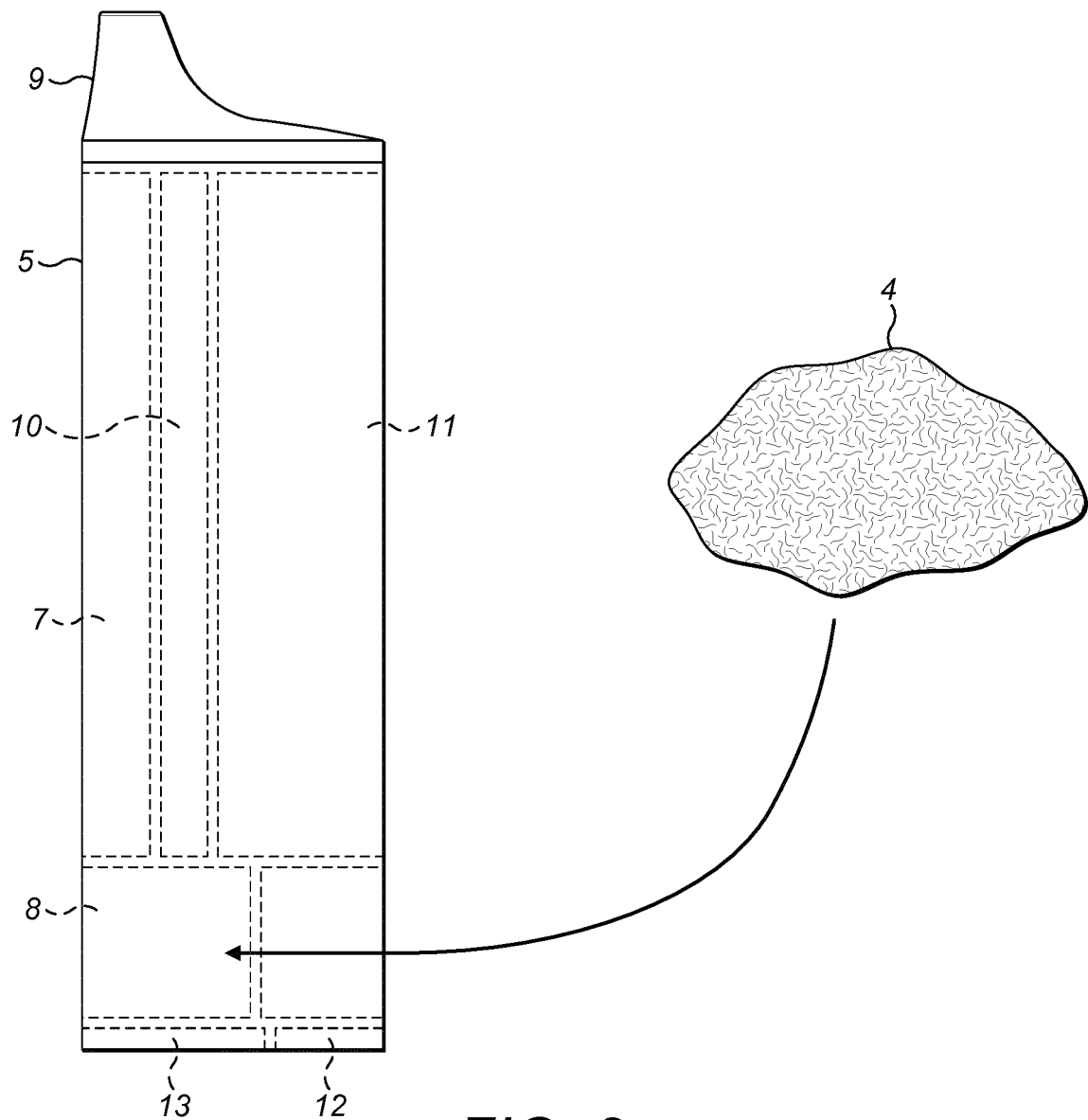
FIG. 2 is a schematic diagram showing a device for generating vapour that can be employed in the system of the invention, with an apparatus according to the invention shown in schematic form also.

As can be seen from FIG. 2, the device 5 has a mouthpiece 9 which communicates with an airflow passage 10 which connects to a heater and chamber 8. A battery 11 powers the circuitry 7 and the heater 8 and in this example the battery 11 is rechargeable through a charging port 12. A lid 13 covers the heater 8 and allows access by a user for insertion of consumable 4.

The apparatus 1 of the invention has circuitry 2 which has a data storage component for storing data associated with the consumable. That data is used to control the operation of the device 5 as will be described below. The circuitry 2 may contain passwords and identification codes to enable only secure communication via the antenna 3 with any device 5. The data stored on the circuitry 2 may be rewritable or may be configured to be read only once.

In use a consumer purchases a consumable or consumables 4 within a package in the form of a case 15 and the apparatus 2 communicates via antenna 3 with a device 5 via its antenna 6. Data on the circuitry 2 is read by the device 5 and, if it is determined by the device 5 that the data is valid, the device 5 will receive and record data in relation to activation of the device 5 and in relation to operation of the device 5 in respect of the consumable 4 that is associated with the data on the circuitry 2. Once data has been read from the circuitry 2, the data on it may be deleted or blocked so that it can only be used once, such that an unwanted party is blocked from using the apparatus 1 to subsequently identify consumables that are not necessarily authorized or safe, reducing the possibility of counterfeiting.

The data that is provided in relation to operation of the device can for example indicate that the consumable being inserted is tobacco based and that one case 15 of consumable products has 12 units of consumable product 4 in it. Each unit can be configured to allow a certain amount (five minutes, for example) of use, or a certain number of puffs (for example ten) per unit. The device 5 is then activated for the insertion consecutively of 12 consumable units and then, after insertion of each, is enabled for, for example, five minutes of use or ten puffs, etc. After that time (or number of puffs, etc.) further operation of the device 5 is blocked until the new consumable is inserted or, after all 12 consumables have been used. The device 5 is reactivated by purchase of a replacement set of consumables and a subsequent apparatus 2 being employed to reactive the device 5. In this way the data allows control of a first counter which counts the level of usage of a consumable for one vapour generating session and allows operation of the device to be prevented after a predetermined the level of usage of the consumable for one vapour generating session and reset of the first counter once data relating to a replacement consumable is provided.

Referring now to the device 5, in use a user activates the device 5 by placing the apparatus 2 adjacent thereto. The user can then insert the consumable 4 into the heater compartment 8 of the device 5. There may optionally be an additional verification of the consumable 4 through a further identifier on that consumable 4, which again can use a wireless connection or could simply be an optical barcode or other identifier. The circuitry 7 on the device 5 then controls operation of the device 5 under the instruction of the user or through detection of a puff being drawn through the mouthpiece 9 or through other components such as a battery consumption sensor to control operation of the heater 8 and the generation of vapour from the consumable 4. The circuitry 7 employs, as part of this control process, operational data it has received from the apparatus 1 such that after a determined period of use, or a determined number of puffs, for example, further operation of the heater is prevented until the consumable 4 has been removed and replaced. The circuitry 7 may employ one or more counters which assist in that control and which have outputs which are used to interact with the operational data and activation data received from the apparatus 1. As described above, a first counter may control the operation of the device 5 for each individual consumable 4 by counting frequency of use or number of puffs, etc. In such a manner, a second counter may have a count which counts the number of consumables that have been used since the device 5 has been activated, and prevents further operation when a certain number of consumables have been used. In this way the data allows control of a second counter which counts the number of consumables that have been used by the device such that the vapour generating device can be used only for a predetermined, fixed, number of consumables until the second counter is reset by the provision of a new data associated with control of activation of the device or data associated with control of the vapour generating device in use, or which counts the level of usage of consumables for plural vapour generating sessions that have been used by the device such that the vapour generating device can be used only for a predetermined, fixed, usage of consumables until the second counter is reset by a provision of new data associated with control of activation of the device or data associated with control of the vapour generating device in use.

As will be appreciated, a number of communication methods can be employed to provide data from the apparatus 1 to the device 5. These can include Wi-Fi standards, Bluetooth communication, amongst other well-known techniques. The apparatus 1, as mentioned previously, may be in the form of an RFID tag which requires no power itself and can be constructed to be positioned at either an external or an internal location in the case 15 for the consumables 4, or can in some circumstances even be applied to an individual consumable (although this is not preferred).

As will be appreciated from the above description, the present invention provides an apparatus which is very flexible in terms of its application and association with individual or plural consumables and yet which can in a very simple and effective way, provide control data to a vapour generating device. In the apparatus in the system of the invention it is possible for a manufacturer or a supplier of a vaporizing device and its consumables to control in a safe and effective manner the type of consumable that can be used by the device 5, and also how vapour is generated consumable to optimize vapour generating and ensure quality and safety.

In an alternative embodiment, the device is operable to have multiple sets of first and second counters so that multiple different types of consumables may be used interchangeably without having to finish a complete package of a first type of consumable before switching to a second type of consumable. For example if a user purchases two packs of consumables of different types (e.g. a first package of 20 tobacco flavoured consumables and a second package of 10 mentholated tobacco flavoured consumables) the user may present the first package to the device and then insert into the device a tobacco flavoured consumable. This causes the device to generate a second counter associated with the first package and to set it to 20. Once that consumable has been fully consumed (using operating parameters selected as appropriate for use in vaporizing a tobacco flavoured consumable) the device decrements the second counter associated with the first package to 19.

The user may then wish to use a mentholated tobacco flavoured consumable. To do this, the user may present to the device the second package. Upon reading the second package, the device may generate an additional second counter associated with the second package and set this to 10. The user then inserts a mentholated tobacco flavour consumable into the device and when the device determines that it has been consumed it decrements the second counter associated with the second package to 9. If the user again then wishes to switch back to the consumables from the first package he/she does this by again presenting the first package to the device. This causes the device to expect a consumable from the first package to be inserted into the device. And hence further operation of the device will use parameters suitable for vaporising a tobacco flavoured consumable. If a new consumable is inserted into the device after consumption of the (second) tobacco flavoured one without presenting a package to the device, the device assumes that the new consumable is from the same package as the preceding one. In principle, the number of different packages that can be used simultaneously is not particularly limited subject to data storage capabilities of the device although in practice a limit of about 10 different packages simultaneously may be appropriate.

In an alternative embodiment in relation to above multiple sets of first and second counters, the device may be capable of recognizing the type of consumable put therein so that the device can judge from which package the consumable has come. In this case the user doesn't need to present each package to the device before switching the type of consumable. This enables the device to decrement each counter automatically without additional effort from the user being required.

The invention claimed is:
1. A vapour generating control apparatus for a vapour generating device which generates vapour through use of a consumable, the apparatus comprising:
   a data storage medium arranged to store data used for control of activation of the device and data used for control of the vapour generating device in use; and a communication unit for communicating with the device such that, in use, both activation and operation of the device can be controlled by the apparatus based on the stored data,
  wherein the apparatus is arranged such that, once the data stored in the data storage medium has been used for control of the vapour generating device, the data is prevented from being used again, and
  wherein the data used for activation of the vapour generating device or the data used for control of the vapour generating device in use allows control of a first counter which counts the level of usage of a consumable for one vapour generating session and allows operation of the device to be prevented after a predetermined level of usage of the consumable for one vapour generating session and reset the first counter once data relating to an authenticated replacement consumable is provided.

2. The apparatus according to claim 1, wherein the communication unit further communicates with the consumable using an identifier of the consumable.

3. The apparatus according to claim 1, wherein the data used for control of the device includes data used for a consumable consumption operation performed by the device.

4. The apparatus according to claim 3, wherein the consumable consumption operation is at least one of:
  operation time of a heater of the vapour generating device;
  operating temperature of a heater of the vapour generating device;
  a puff detection sensor in the vapour generating device;
  a consumable level detection in the vapour generating device;
  a battery consumption and/or charge level detection in the vapour generating device; or
  a detection of replacement of the consumable within the vapour generating device.

5. The apparatus according to claim 1, wherein the data used for control of the vapour generating device further comprises data defining the period of time or number of activations that the vapour generating device is allowed to have.

6. The system according to claim 1, wherein after the predetermined level of usage of the consumable for one vapour generating session has been met, operation of a heater of the device is prevented until the authenticated replacement consumable is provided.

7. The apparatus according to claim 1, wherein the data used for activation of the vapour generating device or the data used for control of the vapour generating device in use allows control of a second counter which counts the number of consumables that have been used by the device such that the vapour generating device can be used only for a predetermined number of consumables until the second counter is reset by a provision of a new data used for control of activation of the device or data associated with control of the vapour generating device in use, or which counts the level of usage of consumables for plural vapour generating sessions that have been used by the device such that the vapour generating device can be used only for a predetermined, fixed, usage of consumables until the second counter is reset by the provision of new data used for control of activation of the device or data used for control of the vapour generating device in use.

8. The apparatus according to claim 1, arranged such that the data stored on the data storage medium is rewritable.

9. A system comprising the apparatus of claim 1, a vapour generating device for receiving signals from the apparatus, and at least one consumable from which the vapour generating device generates vapour in use.

10. The system of claim 9, wherein the apparatus is provided on packaging for the at least one consumable or a material attached in the packaging.

11. The system of claim 9, wherein the consumable comprises at least one of: tobacco, nicotine-containing vaporizable liquid, or vaporizable liquid which does not contain nicotine.

12. The system of claim 9, wherein the apparatus is formed as part of a Radio Frequency Identification, RFID, tag which communicates wirelessly with the vapour generating device to provide the control data to the vapour generating device.

13. The system according to claim 9, wherein the vapour generating device has control unit for controlling components on the vapour generating device based on data communicated from the apparatus.

14. The system according to claim 13, wherein the vapour generating device has a first counter for counting the level of usage of a consumable for one vapour generating session, a second counter for counting the sequential number of consumables that have been placed in the device or the level of usage of the device for a plurality of vapour generating sessions, and the control unit further controls vapour generation in dependence upon the counters.

* * * * *